United States Patent
Kahl et al.

[11] Patent Number: 5,616,771
[45] Date of Patent: Apr. 1, 1997

[54] PREPARATION OF ARYL CHLOROFORMATES

[75] Inventors: Thomas-Michael Kahl, Römerberg; Thomas Wettling, Limburgerhof, both of Germany

[73] Assignee: BASF Aktiengesellschaft, Ludwigshafen, Germany

[21] Appl. No.: 648,892

[22] Filed: May 16, 1996

[30] Foreign Application Priority Data

May 19, 1995 [DE] Germany .................. 195 18 473.4

[51] Int. Cl.$^6$ .................................................. C07C 68/02
[52] U.S. Cl. ........................................................ 558/282
[58] Field of Search .................................... 558/282

[56] References Cited

U.S. PATENT DOCUMENTS

| 3,211,774 | 10/1965 | Wayne . |
| 3,211,775 | 10/1965 | Wayne . |
| 3,211,776 | 10/1995 | Wayne . |
| 3,334,128 | 8/1967 | Brown ..................................... 260/463 |
| 4,085,129 | 4/1978 | Semler et al. . |
| 4,366,102 | 12/1982 | Rauchschwalbe et al. . |
| 5,274,164 | 12/1993 | Wettling et al. . |

FOREIGN PATENT DOCUMENTS

| 080913 | 6/1983 | European Pat. Off. . |
| 2131555 | 12/1971 | Germany . |
| 3000524 | 7/1981 | Germany . |
| 3019526 | 11/1981 | Germany . |
| 4137640 | 5/1993 | Germany . |
| 2108961 | 5/1982 | United Kingdom . |

*Primary Examiner*—Johann Richter
*Assistant Examiner*—Michael G. Ambrose
*Attorney, Agent, or Firm*—Keil & Weinkauf

[57] ABSTRACT

A process for preparing an aryl chloroformate is disclosed that involves the reaction of a phenol with phosgene in the presence of a cyclic urea.

5 Claims, No Drawings

PREPARATION OF ARYL CHLOROFORMATES

The present invention relates to a process for preparing aryl chloroformates by reacting phenols with phosgene in the presence of a cyclic urea.

The preparation of aryl chloroformates by reacting phenols with phosgene in the presence of less than the stoichiometric amounts of a catalyst under elevated pressures is disclosed in U.S. Pat. No. 3,211,774 with dimethylformaide, in U.S. Pat. No. 3,211,775 with polymeric compounds having free secondary or tertiary amino groups, and in U.S. Pat. No. 3,211,776 with amines and ammonium salts, as catalysts.

Reactions of phosgene under pressure are difficult to control in process technology and safety terms and require great technical complexity.

Catalysts used in less than the stoichiometric amounts for reactions under atmospheric pressure are aliphatic amides, disclosed in DE-A 21 31 555, ammonium salts, disclosed in DE-A 30 00 524, phosphines, phosphine oxides and phosphonium salts, disclosed in DE-A 30 19 526, and phosphites, disclosed in DE-A 41 37 640.

These catalysts have the disadvantages of low rates of the phosgene/phenol reaction and increased formation of aryl chlorides during the reaction or distillation, usually combined with inactivation of the catalyst. Furthermore, the disposal of phosphorus-containing distillation residues is made difficult by the formation of phosphoric acid on incineration.

It is an object of the present invention to remedy the above-mentioned disadvantages, in particular to find a process which gives high space-time yields with phosphorus-free catalysts.

We have found that this object is achieved by a novel and improved process for preparing aryl chloroformates of the general formula I

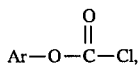

where

Ar is aryl which is unsubstituted or substituted once to five times by $C_1-C_6$alkyl, $C_2-C_6$-alkenyl, $C_3-C_8$-cycloalkyl, $C_4-C_{10}$-cycloalkylalkyl, $C_1-C_6$-haloalkyl, $C_1-C_6$-alkoxy, $C_1-C_4$-alkyl-thio, halogen, cyano, $C_2-C_6$-alkylcarbonyloxy, formyl, $C_2-C_6$-dialkylamino, aryl, aryloxy, arylthio, aryl, $C_7-C_{10}$-aralkyl, $C_7-C_{10}$-aralkoxy, arylsulfonyl and/or $C_7-C_{10}$-aralkylthio and/or once or twice by chloroformyl and/or nitro by reacting phosgene and a phenol of the general formula II

where Ar has the abovementioned meanings, in the presence of a nitrogen-containing compound at from 60° to 180° C. under from 0.01 to 5 bar, wherein the nitrogen-containing compound used is a cyclic urea of the general formula III

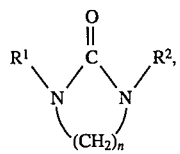

where $R^1$ and $R^2$ are each $C_1-C_4$-alkyl and n is 2 or 3.

The novel process can be carried out as follows:

The phenol II can be reacted with phosgene continuously or batchwise, preferably continuously, in the presence of a cyclic urea III as catalyst at from 60° to 180° C., preferably 80° to 160° C., particularly preferably 100° to 140° C., under from 0.01 to 50 bar, preferably 0.5 to 5 bar, particularly preferably 0.9 to 1 bar, especially atmospheric pressure, preferably in a liquid-phase process, particularly preferably in homogeneous liquid phase such as in an inert solvent or in a melt of the phenol II.

The preferred continuous process can be carried out, for example, in a reaction tube, in a cascade of stirred vessels, in a loop reactor or in a countercurrent column.

The molar ratio of cyclic urea III to phenol II is, as a rule, from 0.001:1 to 0.2:1, preferably 0.002:1 to 0.1:1, particularly preferably 0.005:1 to 0.05:1.

The molar ratio of phosgene to phenol II is, as a rule, from 0.5:1 to 50:1, preferably 1:1 to 2:1, particularly preferably 1:1 to 1.5:1, especially 1:1 to 1.2:1.

Examples of suitable inert solvents are aliphatic and aromatic hydrocarbons such as pentane, hexane, cyclohexane, toluene, xylene or benzene, halogenated hydrocarbons such as trichloroethane, chlorobenzene or dichlorobenzene, or esters such as ethyl acetate or butyl acetate, or the chloroformate of the appropriate phenol.

It is as a rule preferred not to use a solvent and operate only in the melt of the phenol, or to use the chloroformates produced by phosgenation of the described phenols, for example, as solvent. However, the use of a solvent may be advantageous when the melting point of the phenol or the corresponding chloroformate is above the desired reaction temperature and the phenol would, at least at the start of the reaction, react only slowly with the phosgene in the absence of the solvent. The presence of a solvent may also be beneficial to control and dissipate the heat of the exothermic reaction.

The reaction mixture can be worked up, for example, by distillation. As a rule, the distillation residue contains the cyclic urea III which can be used again for another reaction in the novel process.

The substituents Ar, $R^1$, $R^2$ and the index n in the compounds I, II and III have the following meanings:

Ar aryl such as phenyl, 1-naphthyl, 2-naphthyl, 1-anthryl, 2-anthryl and 9-anthryl, preferably phenyl, aryl which is unsubstituted or substituted once to five times by one of the following radicals, $C_1-C_6$-alkyl, preferably $C_1-C_4$-alkyl such as methyl, ethyl, n-propyl, isopropyl, n-butyl, isobutyl, sec-butyl, tert-butyl, $C_2-C_6$-alkenyl, preferably vinyl and allyl, $C_3-C_8$cycloalkyl, preferably $C_4-C_6$-cycloalkyl such as cyclobutyl, cyclopentyl and cyclohexyl, $C_4-C_{10}$-cycloalkylalkyl, preferably $C_6-C_8$-cycloalkylalkyl such as cyclopentylmethyl, cyclohexylmethyl, cyclobutylethyl, cyclohexylethyl, cyclopropylpropyl, cyclobutylpropyl, cyclopentylpropyl and cyclohexylpropyl, $C_1-C_6$-haloalkyl, preferably $C_1-C_4$-haloalkyl, particularly preferably $C_1-C_4$-fluoro- and chloroalkyl such as fluoromethyl, difluoromethyl, trifuloromethyl, chloromethyl, cidhloromethyl, trichloromethyl, 1-chloroethyl, 2-chloroethyl, $C_1-C_6$-alkoxy, preferably $C_1-C_4$-alkoxy such as methoxy, ethoxy, n-propoxy, isopropoxy, n-butoxy, isobutoxy, sec-butoxy, tert-butoxy, $C_1-C_6$-alkylthio, preferably $C_1-C_4$-alkylthio such as methylthio, ethylthio, n-propylthio, isopropylthio, n-butylthio, isobutylthio, sec-butylthio, tert-butylthio, halogen such as fluorine, chlorine, bromine and iodine, preferably fluorine, chlorine, particularly preferably chlorine, cyano, formyl, $C_2$–$C_6$-alkylcarbonyloxy, preferably $C_2$–$C_4$-alkylcarbonyloxy such as acetoxy, propionyloxy, butyryloxy, $C_2$–$C_6$-dialkylamino, preferably di-$C_1$–$C_3$-alkylamino such as N,N-dimethylamino, N,N-diethylamino, N,N-dipropylamino, N,N-di-(1-methylethyl)amino, N-ethyl-N-methylamino, N-methyl-N-propylamino, N-methyl-N-(1-methylethyl)amino, N-ethyl-N-propylamino, N-ethyl-N-(1-methylethyl)amino, N-(1-methylethyl)-N-propylamino, preferably N,N-dimethylamino, N,N-di-ethylamino, in particular N,N-dimethylamino, aryl such as phenyl, 1-napthyl, 2-naphthyl, 1-anthryl, 2-anthryl and 9-anthryl, o-tolyl, m-tolyl and p-tolyl, preferably phenyl, aryloxy such as phenoxy, 1-napthoxy, 2-napthoxy, 1-anthroxy, 0-anthroxy, o-tolyloxy, m-tolyloxy and p-tolyloxy, preferably phenoxy, arylthio such as phenylthio, 1-anpthylthio, 2-naphthylthio, 1-anthrylthio, 2-anthrylthio and 9-anthrylthio, preferably pehnylthio, aroyl such as benzoyl, 1-naphthoyl, 2-naphthoyl, 1-anthracenecarbonyl, 2-anthracenecarbonyl and 9-anthracenecarbonyl, preferably benzoyl, $C_7$–$C_{10}$-aralkyl, preferably $C_7$–$C_8$-phenyl-alkyl such as benzyl, 1-phenethyl, 2-phenethyl, particularly preferably benzyl, $C_7$–$C_{10}$-aralkoxy, preferably $C_7$–$C_8$-phenyl-alkoxy such as benzyloxy, 1-phenethoxy, 2-phenethoxy, arylsulfonyl such as phenylsulfonyl, 1-naphthylsulfonyl, 2-naphthylsulfonyl, 1-anthylsulfonyl, 2-anthrylsulfonyl and 9-anthylsulfonyl, preferably phenylsulfonyl, $C_7$–$C_{10}$-aralkylthio, preferably $C_7$–$C_8$-phenylalkylthio such as benzylthio, 1-phenethylthio, 2-phenethylthio, particularly preferably benzylthio, and/or aryl which is unsubstituted or substituted once or twice by one of the following radicals, chloroformyl, nitro, and in the case of compounds II also in addition one or two hydroxyl groups $R_1$, $R_2$ independently of one another $C_1$–$C_4$-alkyl, preferably $C_1$–$C_2$-alkyl such as methyl, ethyl, n 2 or 3.

Aryl chloroformates I are valuable intermediates, for example in the preparation of dyes such as Sirius dyes (DE-A-23 25 088, Ullmanns Enzyklopadie der technischen Chemie, Volume 4, pages 105, 108 and 109, Urban and Schwarzenberg, 3rd Edition, Berlin-Munich, 1953), for preparing polycarbonate plastics, crop protection agents and for preparing bactericides (DE-A-21 31 555, DE-A-12 13 419 and Ullmanns Enzyklopadie der technischen Chemie, 4th Edition, Volume 9, page 383, Verlag Chemie 1975).

EXAMPLES 9 g (100 mmol) of phosgene were passed over the course of 10 min into the amount of catalyst indicated in Table 1 and 9 g (100 mmol) of phenol at 110° C. Subsequently, over the course of time indicated in the table, 179 g (1900 mmol) of phenol and 198 g (2000 mmol) of phosgene were fed in, reaction was continued for 1 hour and the excess phosgene and dissolved hydrogen chloride were removed by flushing with nitrogen. Distillation resulted in phenyl chloroformate, boiling point 94°–95° C./50 mbar. The distillate was investigated by gas chromatography.

| Example | Catalyst | Conc. a) | Reaction time [h] | Yield after distillation [%] | Composition [GC % areas] Chlorobenzene | Composition [GC % areas] Phenyl chloroformate | Color [APHA] |
|---|---|---|---|---|---|---|---|
| 1 | dimethylformamide | 2 | 5 | 91 | <0.1 | 99.7 | <150 |
| 2 | tetramethylurea | 2 | 7 | 92 | <0.1 | 99.6 | <10 |
| 3 | tetrabutylurea | 2 | 5 | 94 | 0.1 | 99.6 | 30 |
| 4 | triphenylphosphine | 2 | 4 | 92 | 0.5 | 99.3 | 30 |
| 5 | triphenyl phosphite | 2 | 3 | 95 | 0.7 | 99.1 | <10 |
| 6 | dimethylpropyleneurea | 2 | 3 | 96 | — | 99.9 | <10 |
| 7 | residue from Example 2 | — | 9 | 94 | <0.1 | 99.5 | <10 |
| 8 | residue from Example 7 | — | after 14 h | reaction incomplete | — | — | — |
| 9 | residue from Example 3 | — | after 14 h | reaction incomplete | — | — | — |
| 10 | residue from Example 5 | — | 8 | 94 | 1 | 98.8 | <10 |
| 11 | residue from Example 10 | — | after 14 h | reaction incomplete | — | — | — |
| 12 | residue from Example 6 | — | 3.5 | 96 | — | 99.9 | <10 |

-continued

| Example | Catalyst | Conc. a) | Reaction time [h] | Yield after distillation [%] | Chlorobenzene | Phenyl chloroformate | Color [APHA] |
|---|---|---|---|---|---|---|---|
| 13 | residue from Example 12 | — | 4.5 | 97 | — | 99.9 | <10 |
| 14 | dimethylpropyleneurea | 1 | 3.5 | 94 | — | 99.9 | <10 |
| 15 | residue from Example 14 | — | 7 | 94 | — | 99.9 | <10 |
| 16 | dimethylpropyleneurea | 0.5 | 5.5 | 97 | — | 99.9 | <10 |
| 17 | residue from Example 16 | — | after 14 h | reaction incomplete | — | — | — | a) concentration in mol % based on phenol II

We claim:

1. A process for preparing aryl chloroformates of the general formula I $$Ar-O-\overset{\overset{O}{\|}}{C}-Cl, \quad (I)$$

where

Ar is aryl which is unsubstituted or substituted once to five times by $C_1$–$C_6$alkyl, $C_2$–$C_6$-alkenyl, $C_3$–$C_8$-cycloalkyl, $C_4$–$C_{10}$-cycloalkylalkyl, $C_1$–$C_6$-haloalkyl, $C_1$–$C_6$-alkoxy, $C_1$–$C_4$-alkylthio, halogen, cyano, $C_2$–$C_6$-alkylcarbonyloxy, formyl, $C_2$–$C_6$-dialkylamino, aryl, aryloxy, arylthio, aroyl, $C_7$–$C_{10}$-aralkyl, $C_7$–$C_{10}$-aralkoxy, arylsulfonyl or $C_7$–$C_{10}$-aralkylthio and/or once or twice by chloroformyl or nitro by reacting phosgene and a phenol of the general formula II $$AR-OH \quad (II),$$

where Ar has the abovementioned meanings, in the presence of a nitrogen-containing compound at from 60° to 180° C. under from 0.01 to 5 bar, wherein the nitrogen-containing compound used is a cyclic urea of the general formula III

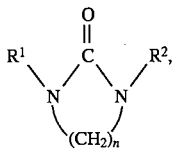

where $R^1$ and $R^2$ are each $C_1$–$C_4$-alkyl and n is 2 or 3.

2. A process for preparing aryl chloroformates as claimed in claim 1, wherein N,N'-dimethylpropylene- or N,N'-dimethylethyleneurea is used as cyclic urea III.

3. A process for preparing aryl chloroformates as claimed in claim 1, wherein the molar ratio of cyclic urea III to phenol II is from 0.001:1 to 0.2:1.

4. A process for preparing aryl chloroformates as claimed in claim 1, wherein the reaction is carried out at from 80° to 160° C.

5. A process for preparing aryl chloroformates as claimed in claim 1, wherein the reaction is carried out under atmospheric pressure.

* * * * *

UNITED STATES PATENT AND TRADEMARK OFFICE
CERTIFICATE OF CORRECTION

PATENT NO.: 5,616,771

DATED: April 1, 1997

INVENTOR(S): KAHL et al.

It is certified that error appears in the above-identified patent and that said Letters Patent is hereby corrected as shown below:

Column 5, claim 1, line 28, "$C_1$-$C_6$alkyl" should be --$C_1$-$C_6$-alkyl--.

Column 5, claim 1, line 28, "$C_3 \propto C_8$-cy-" should be -- $C_3$-$C_8$-cy- --.

Signed and Sealed this

Third Day of June, 1997

Attest:

BRUCE LEHMAN

Attesting Officer

Commissioner of Patents and Trademarks